US007226952B1

(12) United States Patent
Okamoto et al.

(10) Patent No.: US 7,226,952 B1
(45) Date of Patent: Jun. 5, 2007

(54) GEL COMPOSITION AND ITS USE IN COSMETIC COMPOSITIONS AND THE LIKE

(75) Inventors: Mariko Okamoto, Tokyo (JP); Tatsunari Goto, Tokyo (JP); Jean-François Nadaud, Tokyo (JP)

(73) Assignee: L'Oreal, Paris (FR)

( * ) Notice: Subject to any disclaimer, the term of this patent is extended or adjusted under 35 U.S.C. 154(b) by 304 days.

(21) Appl. No.: 09/667,420

(22) Filed: Sep. 21, 2000

(30) Foreign Application Priority Data

Sep. 22, 1999 (JP) ................................. 11-269452

(51) Int. Cl.
*A61K 47/32* (2006.01)
*A61K 9/00* (2006.01)
*A61K 31/74* (2006.01)

(52) U.S. Cl. ................. 514/772.4; 424/400; 424/78.02
(58) Field of Classification Search ............. 514/772.3, 514/772.4; 424/60, 59, 401, 400, 78.02
See application file for complete search history.

(56) References Cited

U.S. PATENT DOCUMENTS 5,567,420 A * 10/1996 McEleney et al. ............ 424/60
5,976,510 A * 11/1999 Cernasov et al. ............. 424/59

FOREIGN PATENT DOCUMENTS

| EP | 0 503 853 | | 9/1992 |
| EP | 0 815 843 | | 1/1998 |
| EP | 1077062 A1 | | 2/2001 |
| JP | 6-211631 | | 8/1994 |
| JP | 7-112915 | | 5/1995 |
| JP | 9-143031 | | 6/1997 |
| JP | 10-101521 | | 4/1998 |
| JP | 11-021227 | * | 1/1999 |
| JP | 11-21227 | | 1/1999 |
| JP | 11021227 | | 1/1999 |
| JP | 11-130631 | | 5/1999 |
| JP | 11-240826 | | 9/1999 |
| JP | 2000-178149 | | 6/2000 |
| JP | 2001064116 | | 3/2001 |

OTHER PUBLICATIONS

English language Derwent Abstract of EP 0 815 843.
Patent Abstracts of Japan, vol. 1995, No. 08, Sep. 29, 1995, JP 07 112915.
English language abstract of JP 6-211631.
English language Derwent Abstract of JP 7-112915.
English language abstract of JP 11-21227.
Database Chemabs, Chemical Abstracts Service, Columbus, OH, US; Database Accession No. 129:293698 CA, XP 0021538456, JP 10 279826.
English-language abstract of JP 2001064116.
English-language abstract of EP 1077062 A1.
Computer generated translation of JP 9-143031 by Japanese Patent Office.
Computer generated translation of JP 11-130631 by Japanese Patent Office.
JP-AH7-112915 computer generated translation of JP 7-112915, published May 2, 1995.

* cited by examiner

*Primary Examiner*—Michael G. Hartley
*Assistant Examiner*—Blessing Fubara
(74) *Attorney, Agent, or Firm*—Finnegan Henderson Farabow Garrett & Dunner, L.L.P.

(57) ABSTRACT

A gel composition and cosmetic composition and the like that can excel in pigment and/or filler uniformity and stability and can have a good outer appearance even when further comprising a relatively large amount of pigments. A gel composition is formed by combining at least one ingredient chosen from pigments and fillers, wherein the at least one ingredient has been surface-treated by at least one water-repellent oil-repellent agent, and at least one gelling agent comprising at least one polyacrylamide-based polymer.

33 Claims, No Drawings

GEL COMPOSITION AND ITS USE IN COSMETIC COMPOSITIONS AND THE LIKE

The present invention relates to gel compositions with a novel texture, and particularly relates to gel compositions comprising a relatively high amount of at least one pigment and/or filler, suitable for use in cosmetic compositions and in external agents for the skin. Additionally, the invention relates to cosmetic compositions that can be in the form of a makeup, sun care or skin care composition or an external agent for the skin formulated by using this gel composition.

While various agent formats have been used conventionally in the field of cosmetics, cream or lotion type formats can lack a feeling of refreshment and tend to be sticky, and therefore might not be suited to regions or seasons with high-temperature, high-humidity climates, such as the summers in Japan. However, gel compositions which are generally known as gels are widely used as agent formats which have an abundant sense of refreshment.

However, although it is often desirable to add a relatively large amount of pigments and/or fillers depending on the type of cosmetic composition, if pigments and/or fillers are included in large amounts in a gel base, the pigments and/or fillers may not be uniformly dispersed in the gel base due to compatibility problems. Accordingly, the appearance of the gel may become non-uniform, similar to the surface pattern of marble.

Additionally, while water-soluble polymers with gelling ability are used for the formulation of gels, the particle supporting network structure formed by the polymers can become unstable after the passage of a few days to a few weeks due to an ionization effect, and the overall quality of the gel product can be decreased.

Furthermore, while gum-based gels using xanthan gum as the water-soluble polymer are known, these gels tend to be sticky, and may not have a sufficient sense of refreshment.

Moreover, conventional gel compositions can also have less fitness to skin and be less easily applied in comparison to other formats.

It would be advantageous to discover gel compositions comprising exceptional pigment and/or filler dispersability and stability, having a good appearance, providing a sense of coolness and a sense of refreshment without stickiness, and having exceptional fitness and applicability to skin in comparison with conventional gel compositions.

Upon performing diligent research in view of the above situation, the present inventors discovered unexpectedly that it is possible to obtain an excellent gel composition that overcomes at least one of the above-described drawbacks by surface-treating the pigment and/or filler with a water-repellent and oil-repellent agent and by using a gelling agent comprising a polyacrylamide-based polymer.

Accordingly, the present invention can provide a gel composition which has at least one of the following characteristics: (1) excels in pigment and/or filler dispersability and stability; (2) has a good outer appearance in comparison to conventional gel compositions; and (3) can possess both (1) and (2) even when comprising a relatively large amount of pigments.

Another purpose of the invention is to offer gel compositions that have at least one of the following characteristics: (1) minimize stickiness, (2) have a sense of coolness and/or refreshment; (3) have exceptional fitness to the skin, and (4) have exceptional applicability to the skin.

The present invention provides a gel composition comprising:

(1) at least one gelling agent comprising at least one polyacrylamide-based polymer, and (2) at least one ingredient chosen from pigments and fillers, wherein the at least one ingredient has been surface-treated by at least one water-repellent and oil-repellent agent.

The present invention also offers cosmetic compositions and external agents for skin using the above-described gel composition.

Furthermore, the present invention relates to a process for stabilizing a gel composition comprising adding to the gel composition:

(1) at least one gelling agent comprising at least one polyacrylamide-based polymer, and (2) at least one ingredient chosen from pigments and fillers, wherein the at least one ingredient has been surface-treated by at least one water-repellent and oil-repellent agent.

In the context of the present invention, the term "gel" refers to what those skilled in the art understand by the term, and in general refers to a composition having a viscosity range, which is preferably in the range of about 10 scale units (317 mPa·s) to about 90 scale units (3595 mPa·s), such as about 60 scale units (2336 mPa·s) to about 80 scale units (3178 mPa·s), as measured by a Contraves viscometer TV (Contraves Industrial Products Ltd.; Mobile 3; at 25° C.).

The at least one ingredient chosen from pigments and fillers, used in the gel composition of the present invention, may be of any type conventionally used or usable in the fields of cosmetics and dermatology, examples of which include inorganic pigments, such as extender pigments, coloring pigments, and whitening pigments; organic pigments; pearlescent gloss pigments; macromolecular powders; and functional pigments. More specific examples include talc, mica, kaolin, calcium carbonate, magnesium carbonate, silicic anhydride, aluminum silicate, magnesium silicate, calcium silicate, aluminum oxide, barium sulfate, red iron oxide, yellow iron oxide, black iron oxide, chrome oxide, ultramarine blue, prussian blue, carbon black, zinc oxide, mica titanium, fish scale flakes, bismuth oxychloride, boron nitride, nylon powder, silk powder, tar pigments, natural pigments and titanium oxide, such as amorphous or rutile type and/or anatase type crystals.

In the context of the present invention, the term "water-repellent and oil-repellent" refers to the property that the treated at least one pigment and/or filler is resistant to water and oil. The degree of the water and oil repellence which may be used in the present invention is similar to that taken generally by those skilled in the art. The degree of the water and oil repellence may be such that the minimum angle of contact of a water or oil (liquid petrolatum) droplet on a water- and oil-repellent surface can be at least about 90° for both water and oil, such as at least about 110° for oil and such as at least about 120° for water.

As the water-repellent and oil-repellent agent for surface-treating the above-described pigment, it is possible to use any type which has conventionally been used to confer water repellence and oil repellence to pigments. For example, in the present invention, fluorine compounds can be used.

Representative fluorine compounds which are conventionally used and can act as water-repellent and oil-repellent agents include compounds having perfluoroalkyl groups such as perfluororalkyl phosphates, perfluoroalkyl silanes, perfluoroalkyl silazanes, polyhexafluoropropylene oxides, perfluoroalkyl-group-containing organosiloxanes, per-fluoropolyethers, perfluoro alcohols, perfluoroalkylacrylate polymers, and derivatives thereof.

In the present invention, perfluoroalkyl phosphates, which can provide for a uniform and stable dispersement of pigments within the formulation of a gel composition, and perfluoroalkyl silanes, which can be somewhat less capable in terms of pigment dispersability but can have exceptional compatibility with other constituents in the case of a cosmetic composition, can be used. Representative perfluoroalkyl phosphates that can be used include those that are described in Japanese Patent Application, Second Publication No. Hei 5-86984, the disclosure of which is incorporated by reference herein. Additionally, the perfluoroalkyl phosphate-diethanol amine salt marketed by Asahi Glass as AsahiGuard AG530, and perfluoroalkyl silane coupling agents, such as LP-IT and LP-4T of Shin-Etsu Silicone, can be used.

Additional representative water-repellent and oil-repellent agents include amino acid compounds, particularly acylated amino acids or their salts. Among these types of water-repellent oil-repellent agents, the N-mono-long chain acyl basic amino acid disclosed in Japanese Patent Application, First Publication No. Sho 61-10503 is known, the disclosure of which is incorporated by reference herein. Here, as examples of long-chain acyl groups, there are $C_8$–$C_{22}$ saturated and unsaturated, straight and branched aliphatic acyl groups, specifically 2-ethylhexanoyl, caproyl, lauroyl, myristoyl, palmitoyl, stearoyl and cocoyl. Moreover, as disclosed in Japanese Patent Application, Second Publication No. Hei 1-50201, the disclosure of which is incorporated by reference herein, metal salts of N-acyl amino acids, and in particular salts of Al, Mg, Ca, Zn, Zr, Ti or the like can also be suitably used. Here, as examples thereof, there are salts of N-acyl-N-methylglycine, N-acyl-N-β-alanine, N-acyl-N-glutamic acid and the like. Because these acylated amino acids are less oil-repellent than the above-mentioned treatment by fluorine compounds, it would be advantageous to use the above-described compounds containing perfluoroalkyl groups as water-repellent oil-repellent agents in the present invention.

The above-described surface treatment of the pigment and/or filler can be performed by any method, such as by physical adsorption of compounds onto the pigment and/or filler surface, by chemical bonding with functional groups on the pigment and/or filler surface, and by physical methods such as mechanofusion. In particular, surface treatment by perfluoroalkyl phosphate-diethanolamine salts has conventionally been performed by adding water thereto and stirring, then mixing this into a slurry formed by adding water to the pigment and/or filler to form an emulsion, then heating as needed and letting stand to destroy the emulsion, and finally cleansing, filtering and drying. Additionally, surface treatment by perfluoroalkyl silane is usually performed by activating the surface of the pigment and/or filler by a plasma treatment, heat treatment or hydrothermal treatment, then baking the perfluoroalkyl silane at above its melting point.

The above-described surface-treated pigment and/or filler present in the gel composition of the invention can be present in the composition in an amount generally ranging from 0.1%–20%, by weight relative to the total weight of the composition, such as from 0.5%–10%.

While the pigments and/or fillers contained in the gel composition of the present invention are basically those which have been surface-treated as described above, untreated pigments and/or fillers can be added as long as the amount is within a range such as to retain the at least one of the effects such as pigment and/or filler dispersability and uniformity of the gel compositions of the present invention. Generally, the amount of untreated pigment and/or filler present in the gel composition is a maximum of 5% by weight relative to the total weight of the composition.

A polyacrylamide-based polymer in an amount generally ranging from 1.0–80.0 wt % with respect to the entire weight of the gelling agent is present in the gelling agent used in the invention. This polyacrylamide-based polymer can, for example, have a number average molecular weight of approximately 1000–1,000,000. Additionally, the polyacrylamide polymer can, aside from being polyacrylamide itself, be a derivative thereof, and can be a mixture of a plurality of types of polymers, and can also be a copolymer with acrylamide and its derivatives as monomers.

Additionally, the above-mentioned gelling agent should generally comprise a at least one ingredient chosen from hydrocarbons and non-ionic surfactants in addition to the polyacrylamide-based polymer. As the hydrocarbon, it is possible to use various types, for example isoparaffin, petrolatum, ceresin and squalane, with $C_4$–$C_{20}$ isoparaffins being especially suitable for use. The content of the hydrocarbon should generally range from 1.0–60.0 wt % of the gelling agent.

Additionally, the non-ionic surfactant may be of any type, such as polyoxyethylene alkyl ($C_{12}$–$C_{14}$) ethers and polyoxyethylene sorbitan fatty acid esters. The content of the non-ionic surfactant should generally range from 0.1–20.0 wt % of the gelling agent.

Representative gelling agents include those marketed by Seppic under the trade names Sepigel 305, Sepigel 501, Sepigel 600, etcetera. Sepigel 305 is a mixture containing approximately 40% polyacrylamide, approximately 24% $C_{13}$–$C_{14}$ isoparaffin and approximately 6% Laureth-7 (here, Laureth-7 is a non-ionic surfactant having the formula $C_{12}H_{25}$—$(OCH_2CH_2)_n$—$OH$, wherein n has an average value of 7). Sepigel 600 is a mixture of a acrylamide/acrylamide-2-propane sulfonate copolymer, isohexadecane and polysorbate 80 (polyoxyethylene sorbitan mono-oleate (20 EO)).

A suitable gelling agent comprising a polyacrylamide-based polymer which can be used in accordance with the present invention is for example disclosed in EP 0 503 853 (Scott Bader Company Ltd.), the disclosure of which is incorporated by reference herein.

The above-described gelling agent can be present in the gel composition in an amount generally ranging from 0.1–10 wt %, such as from 0.1–5 wt %.

As mentioned above, while non-ionic surfactants can be included in the above-mentioned gelling agent, the gel composition according to the present invention generally should not contain surfactants other than the surfactants that are purposefully included in the gel composition.

The gel composition according to the present invention can be an aqueous gel, comprising no oils or only a small amount of oils (a maximum of 10 wt %), such as a gel comprising aqueous constituents in an amount exceeding at least 50 wt %. This type of aqueous gel composition has at least one of the following characteristics: an abundant sense of refreshment, a fresh feel of use, and particularly suited to formulation of cosmetic compositions for summer use or for use on oily skin.

The present invention also relates to a cosmetic composition and/or an external agent for the skin comprising the above-described gel composition.

The cosmetic composition in accordance with the invention can have any mode of use, but, in particular, can be directed at cosmetic compositions for makeup, sun care, skin care, and hair care. The cosmetic compositions for the make-up can be those for the makeup of the body skin such as face, lips, eyes and so on, and also of the body growths such as nails, hair and so on.

Furthermore, the cosmetic composition in accordance with the invention can take the form of a foundation, a lip product, a blush, an eye-shadow, an eyeliner, a concealer, a mascara, a nail enamel and so on.

This cosmetic composition or external agent for skin can further comprise at least one additive such as the usual active ingredients in cosmetic products and external skin products.

Representative additives that can be used in the cosmetic composition and external agent for skin according to the present invention include organic solvents, softening agents, anti-oxidants, anti-free radical agents, opacifiers, stabilizers, emollients, defoaming agents, humectants, vitamins, fragrances, preservatives, sequestering agents, polymers other than the above-described gelling agents, basic and acidic agents, dyes, self-tanning agents, and conventional cosmetic and dermatological adjuvants selected from among any other ingredients that are normally used in the field of cosmetic and/or dermatology.

The types and/or amounts of the ingredients added in this way can be selected by a person skilled in the art with care such as not to have a substantially detrimental effect on the gel composition of the present invention.

Herebelow, the present invention shall be explained in detail by means of examples, but it should be recognized that the present invention is not restricted by these examples in any way. In the following notation, % indicates wt % unless another definition is given.

EXAMPLE 1

In order to confirm the effects of the combination of a surface-treated pigment and/or filler and gelling agent used in the gel composition according to the present invention, a pigment treated with silicone and an untreated pigment were prepared. Additionally, a carobxyvinyl polymer and acrylate/$C_{10}$–$C_{30}$ alkyl acrylate crosslinked polymer which are commonly used water-soluble polymer gelling agents were employed aside from the polyacylamide-based gelling agent of the present invention. Gel compositions 1–5 were formulated; only Gel composition 1 falls within the scope of the present invention.

To evaluate the texture and stability of gel compositions 1–5, the appearance and uniformity were compared, and the stability was studied after storage for 2 months at 45° C. Furthermore, to evaluate the lasting effects and sense of application, tests were performed on the ease of application to the skin, sense of refreshment, sense of coolness, cosmetic stay and pleasantness with respect to female panelists.

The results of the above-described test are shown in the following table.

TABLE 1

| Gel Composition | 1 | 2 | 3 | 4 | 5 |
| --- | --- | --- | --- | --- | --- |
| Polyacrylamide-based polymer* | + | | | + | + |
| Carboxyvinyl polymer | | + | | | |
| Acrylate-based cross-linked polymer** | | | + | | |
| Perfluoroalkyl phosphate treated pigment | + | + | + | | |
| Untreated pigment | | | | + | |
| Silicone-treated pigment | | | | | + |
| Texture/Stability | very good | poor | poor | good | good |
| Lasting/Sense of application | good | good | good | poor | fair |

In the above table, "+" indicates that the gel composition contains that ingredient.
Additionally, "*" indicates Sepigel 305 and "**" indicates an acrylate/$C_{10}$–$C_{30}$ alkyl acrylate cross-linked polymer.

From the results shown in the above table, it can be seen that the gel composition 1 obtained by combining a surface-treated pigment and a gelling composition in accordance with the present invention excels in both texture/stability and lasting/sense of application in comparison to the comparative gel compositions 2–5.

EXAMPLE 2

Gel compositions according to the present invention containing the following various compositions were prepared.

| Gel Foundation | |
| --- | --- |
| Glycerin | 10% |
| Preservative | 2% |
| Sepigel 305 | 2% |
| Perfluoroalkyl sulfonate treated pigment | 9% |
| Cyclopentasiloxan | 15% |
| Tocopheryl acetate | 0.5% |
| Purified water | balance |
| Sun Care Gel | |
| Glycerin | 5% |
| Preservative | 2% |
| Sepigel 305 | 2% |
| Perfluoroalkyl phosphate treated pigment | 9% |
| UV absorbent | 1% |
| Cyclopentasiloxane | 15% |
| Tocopheryl acetate | 0.5% |
| Purified water | balance |
| Gel Foundation | |
| Glycerin | 2% |
| Preservative | 0.8% |
| Sepigel 305 | 2% |
| Cyclopentasiloxane | 12% |
| Tocopheryl acetate | 0.5% |
| Cyclopentasiloxane/dimethiconol | 0.5% |
| Biosaccharide gum-1 | 2% |
| Acylated amino acid salt treated pigment*** | 9% |
| Purified water | balance |
| Gel Foundation | |
| Glycerin | 2% |
| Preservative | 0.8% |
| Sepigel 305 | 2% |
| Cyclopentasiloxane | 12% |
| Tocopheryl acetate | 0.5% |
| Cyclopentastsiloxane/dimethiconol | 0.5% |
| Biosaccharide gum-1 | 2% |
| Perfluoroalkylsilane treated pigment**** | 7% |
| Untreated pigment | 2% |
| Purified water | balance |

-continued

| Gel Foundation | |
|---|---|
| Glycerin | 2% |
| Preservative | 0.8% |
| Sepigel 600 | 2% |
| Cyclopentasiloxane | 12% |
| Tocopheryl acetate | 0.5% |
| Cyclopentasiloxane/dimethiconol | 0.5% |
| Biosaccharide gum-1 | 2% |
| $C_{9-15}$ fluoroalcohol phosphate treated pigment | 9% |
| Purified water | balance |

***Sodium N-acyl-L-glutamate was used as an acylated amino acid salt.
****$CF_3(CF_2)_7CH_2CH_2$—$Si(OCH_3)_3$ was used as the perfluoroalkylsilane.

The above-described gel compositions all had stable and uniformly dispersed pigments.

EXAMPLE 3

The following gel foundation A was further formulated as a gel composition of the present invention, and a comparison test was performed with regard to practical properties with a gel foundation by Kanebo Ltd. (Company K) called "Revue Esthecouture, gel foundation."

| Gel Foundation A | |
|---|---|
| Glycerin | 2% |
| Preservative | 0.8% |
| Sepigel 305 | 2% |
| Cyclopentasiloxane | 12% |
| Tocopheryl acetate | 0.5% |
| Cyclopentasiloxane/dimethiconol | 0.5/ |
| $C_{9-15}$ fluoroalcohol phosphate treated titanium dioxide | 6.21% |
| $C_{9-15}$ fluoroalcohol phosphate treated yellow iron oxide | 0.51% |
| $C_{9-15}$ fluoroalcohol phosphate treated red iron oxide | 0.18% |
| $C_{9-15}$ fluoroalcohol phosphate treated black iron oxide | 0.1% |
| Biosaccharide gum-1 | 2% |
| Purified water | balance |

The present test was performed by handing 11 masked female panelists two types of products and having them evaluate the practical properties. That is, each panelist took each product in hand to evaluate the fluidity and touch, then applied separate products on the right and left sides of their faces to evaluate the texture, state of application, uniformity and cosmetic finish of each product.

As a result of the above-described comparison tests, both products had fluidity and slight oiliness when taken into the hand, but this sensation was slightly stronger in the foundation A of the present invention which has a wet feeling. Perhaps due to this wet effect, with regard to the applicability, the foundation A of the present invention had good smoothness and spread and was easy to apply, while the gel foundation of Company K dried quickly, did not slide, and had a tendency to become fluffy.

Additionally, while the foundation A of the present invention could easily be spread uniformly over the skin, a large amount of the gel foundation of Company K was required in order to be able to apply uniformly over the entire face without feeling any friction.

Furthermore, the sense of use was extremely good during application and after application in the case of the gel foundation A of the present invention, but the comparison product had 7 subjects experiencing discomfort during application (dryness, catching, and irritation) and 3 subjects experiencing discomfort even after application (pulling and irritation).

Additionally, with regard to the cosmetic finish, the gel foundation A of the present invention was evaluated as having excellent coverage (8 out of 11 subjects), being uniform (6 out of 11 subjects) and matted (7 out of 11 subjects).

Furthermore, the gel foundation excelled with regard to fixing/blotting of blotches and freckles, while the comparison product was evaluated as making hairs and pores more conspicuous.

In this way, the gel foundation A of the present invention was found to excel over the commercially available product from Company K with regard to texture, applicability, uniformity, sense of use and cosmetic finish.

EXAMPLE 4

As in Example 3, a gel foundation B of the following composition was further prepared as a gel composition of the present invention, and a practical property test was performed in comparison with the same gel foundation of Company K which was evaluated in Example 3.

| Gel Foundation B | |
|---|---|
| Glycerin | 2% |
| Preservative | 0.8% |
| Sepigel 305 | 2% |
| Cyclopentasiloxane | 12% |
| Tocopheryl acetate | 0.5% |
| Cyclopentasiloxane/dimethiconol | 0.5% |
| $C_{9-15}$ fluoroalcohol phosphate treated titanium dioxide | 5.21% |
| $C_{9-15}$ fluoroalcohol phosphate treated yellow iron oxide | 0.51% |
| $C_{9-15}$ fluoroalcohol phosphate treated red iron oxide | 0.18% |
| $C_{9-15}$ fluoroalcohol phosphate treated black iron oxide | 0.1% |
| Perfluoroalkylethyl phosphate treated titanium nano-oxide (rutile type) (average size 50 nm; Cl 77891) | 3% |
| Biosaccharide gum-1 | 2% |
| Purified water | balance |

The practical properties were evaluated by 11 female panelists as in Example 3. As a result of the above-described comparison tests, both products had fluidity and slight oiliness when taken into the hand, but this sensation was slightly stronger in the foundation B of the present invention which has a wet feeling. Consequently, with regard to the applicability, the foundation B of the present invention had good smoothness and spread and was easy to apply, while the gel foundation of company K dried quickly, did not slide, and had a tendency to become fluffy.

Additionally, while the foundation B of the present invention could easily be spread uniformly over the skin, a large amount of the gel foundation of Company K was required in order to be able to apply uniformly over the entire face without feeling any friction.

Furthermore, the sense of use was extremely good during application and after application in the case of the gel foundation B of the present invention, but the comparison product had 2 subjects experiencing dryness and catching during application and experiencing pulling after application.

Additionally, with regard to the cosmetic finish, the gel foundation B of the present invention was evaluated as having excellent coverage (6 out of 11 subjects), being uniform (6 out of 11 subjects) and matted (3 out of 11 subjects).

Furthermore, the gel foundation excelled with regard to fixing/blotting of blotches and freckles, while the comparison product was evaluated as making hairs and pores more conspicuous.

In this way, the gel foundation B of the present invention was found to excel over the commercially available product from Company K with regard to texture, applicability, uniformity, sense of use and cosmetic finish.

What is claimed is:

1. A gel composition comprising:
   (1) at least one gelling agent comprising at least one polyacrylamide-based polymer, and
   (2) at least one ingredient surface treated with at least one fluorine compound, wherein the at least one ingredient is chosen from pigments and fillers.

2. A composition according to claim 1, wherein said at least one ingredient is chosen from inorganic pigments, organic pigments, pearlescent gloss pigments, macromolecular powders, and functional pigments.

3. A composition according to claim 2, wherein said at least one ingredient is chosen from extender pigments, coloring pigments, and whitening pigments.

4. A composition according to claim 1, wherein said at least one ingredient is chosen from talc, mica, kaolin, calcium carbonate, magnesium carbonate, silicic anhydride, aluminum silicate, magnesium silicate, calcium silicate, aluminum oxide, barium sulfate, red iron oxide, yellow iron oxide, black iron oxide, chrome oxide, ultramarine blue, prussian blue, carbon black, titanium oxide, zinc oxide, mica titanium, fish scale flakes, bismuth oxychloride, boron nitride, nylon powder, silk powder, tar pigments and natural pigments.

5. A composition according to claim 1, wherein the at least one fluorine compound is chosen from compounds having perfluoroalkyl groups.

6. A composition according to claim 5, wherein the at least one fluorine compound is chosen from perfluoroalkyl phosphates, perfluoroalkyl silanes, perfluoroalkyl silazanes, polyhexafluoropropylene oxides, perfluoroalkyl-group-containing organosiloxanes, per-fluoropolyethers, perfluoro alcohols, perfluoroalkylacrylate polymers, and derivatives thereof.

7. A composition according to claim 6, wherein the at least one fluorine compound is chosen from perfluoroalkyl phosphates and perfluoroalkyl silanes.

8. A composition according to claim 7, wherein the perfluoroalkyl phosphates are chosen from perfluoroalkyl phosphate diethanolamine salts.

9. A composition according to claim 7, wherein the perfluoroalkyl silanes are chosen from silane coupling agents.

10. A composition according to claim 1, wherein the at least one ingredient is present in an amount ranging from 0.1%–20% by weight, relative to the total weight of the composition.

11. A composition according to claim 10, wherein the at least one ingredient is present in an amount ranging from 0.5%–10% by weight, relative to the total weight of the composition.

12. A composition according to claim 1, further comprising, in a maximum amount of 5% by weight relative to the total weight of the composition, at least one second ingredient chosen from pigments and fillers, said pigments and fillers not having been surface-treated.

13. A composition according to claim 1, wherein the at least one polyacrylamide-based polymer is chosen from polyacrylamides.

14. A composition according to claim 13, wherein the at least one polyacrylamide-based polymer is chosen from acrylamide/acrylamide-2-methylpropane sulfonate copolymers.

15. A composition according to claim 1, wherein the at least one polyacrylamide-based polymer is present in an amount ranging from 1.0%–80.0% by weight relative to the total weight of the at least one gelling agent.

16. A composition according to claim 1, wherein the at least one gelling agent further comprises at least one compound chosen from hydrocarbons and non-ionic surfactants.

17. A composition according to claim 16, further wherein said composition contains no other surfactant.

18. A composition according to claim 16, wherein the hydrocarbons are chosen from isoparaffins, petrolatum, ceresin and squalane.

19. A composition according to claim 18, wherein the isoparaffins are chosen from $C_4$–$C_{20}$ isoparaffins.

20. A composition according to claim 16, wherein the hydrocarbons are present in an amount ranging from 1.0%–60.0% by weight relative to the total weight of the at least one gelling agent.

21. A composition according to claim 16, wherein the non-ionic surfactants are chosen from polyoxyethylene alkyl ($C_{12}$–$C_{14}$) ethers and polyoxyethylene sorbitan fatty acid esters.

22. A composition according to claim 16, wherein the non-ionic surfactant is present in an amount ranging from 0.1%–20.0% by weight relative to the total weight of the at least one gelling agent.

23. A composition according to claim 1, wherein the at least one gelling agent is present in an amount ranging from 0.1%–10% by weight relative to the total weight of the composition.

24. A composition according to claim 23, wherein the at least one gelling agent is present in an amount ranging from 0.1%–5% by weight relative to the total weight of the composition.

25. A composition according to claim 1, wherein the gel composition is an aqueous gel chosen from aqueous gels comprising no oils and aqueous gels comprising oils present in a maximum amount of 10% by weight relative to the total weight of the composition.

26. A composition according to claim 1, wherein the gel composition is an aqueous gel comprising aqueous constituents in an amount exceeding at least 50% by weight relative to the total weight of the composition.

27. A cosmetic composition comprising a gel composition comprising:
   (1) at least one gelling agent comprising at least one polyacrylamide-based polymer, and
   (2) at least one ingredient surface treated with at least one fluorine compound, wherein the at least one ingredient is chosen from pigments and fillers.

28. A cosmetic composition according to claim 27 further comprising at least one additive chosen from organic solvents, softening agents, anti-oxidants, anti-free radical agents, opacifiers, stabilizers, emollients, defoaming agents, humectants, vitamins, fragrances, preservatives, sequestering agents, polymers other than said at least one polyacrylamide-based polymer, basic and acidic agents, dyes, self-tanning agents, and other conventional cosmetic and dermatological adjuvants.

29. An external agent for the skin comprising a gel composition comprising:
   (1) at least one gelling agent comprising at least one polyacrylamide-based polymer, and (2) at least one ingredient surface treated with at least one fluorine compound, wherein the at least one ingredient is chosen from pigments and fillers.

30. A makeup, a sun care, a skin care or a hair care composition comprising a gel composition comprising:
(1) at least one gelling agent comprising at least one polyacrylamide-based polymer, and
(2) at least one ingredient surface treated with at least one fluorine compound, wherein the at least one ingredient is chosen from pigments and fillers.

31. A composition according to claim 30, wherein the makeup is for the face, lips, eyes, nails or hair.

32. A foundation, a lip product, a blush, an eye-shadow, an eyeliner, a concealer, a mascara, or a nail enamel comprising a gel composition comprising:

(1) at least one gelling agent comprising at least one polyacrylamide-based polymer, and
(2) at least one ingredient surface treated with at least one fluorine compound, wherein the at least one ingredient is chosen from pigments and fillers.

33. A process for stabilizing a gel composition comprising including in said gel composition an effective amount of:
(1) at least one gelling agent comprising at least one polyacrylamide-based polymer, and
(2) at least one ingredient surface treated with at least one fluorine compound, wherein the at least one ingredient is chosen from pigments and fillers.

\* \* \* \* \*